US00PP33840P2

(12) United States Plant Patent
Kogut

(10) Patent No.: US PP33,840 P2
(45) Date of Patent: Jan. 11, 2022

(54) ***THUJA* PLANT NAMED 'LEPRECHAUN'**

(50) Latin Name: ***Thuja standishii* x *plicata***
Varietal Denomination: Leprechaun

(71) Applicant: Frank J. Kogut, Meriden, CT (US)

(72) Inventor: Frank J. Kogut, Meriden, CT (US)

(73) Assignee: Brian Kogut, Meriden, CT (US)

( * ) Notice: Subject to any disclaimer, the term of this patent is extended or adjusted under 35 U.S.C. 154(b) by 0 days.

(21) Appl. No.: 17/176,980

(22) Filed: Feb. 16, 2021

(51) Int. Cl.
*A01H 5/12* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

(56) References Cited

PUBLICATIONS

U.S. Trademark to 'Lucky Leprechaun', U.S. Appl. No. 88/305,962, filed Feb. 18, 2019.*

* cited by examiner

*Primary Examiner* — Anne Marie Grunberg
(74) *Attorney, Agent, or Firm* — Penny J. Aguirre

(57) ABSTRACT

A new cultivar of *Thuja* plant named 'Leprechaun' that is characterized by its slow growing and compact plant habit, its foliage that is soft in texture and dark green in color, its very good cold hardiness without winter foliage bronzing (withstood −20° F.), and its small mature plant size; reaching an average of 2.74 m in height and 1.52 m in width.

2 Drawing Sheets

Botanical classification: *Thuja standishii* x *plicata*.
Varietal denomination: 'Leprechaun'.

BACKGROUND OF THE INVENTION

The present invention relates to a new and distinct cultivar of *Thuja standishii* x *plicata* and will be referred to hereafter by its cultivar name, 'Leprechaun'. 'Leprechaun' represents a new cultivar of western red cedar, an evergreen tree grown for landscape use and particularly useful for hedging.

The Inventor discovered the new cultivar in spring of 2014 in a production field of *Thuja standishii* x *plicata* 'Green Giant' (not patented) in Enfield, Conn. The production field had been planted with plants derived from stem cuttings of 'Green Giant' and therefore 'Leprechaun' arose as a naturally occurring branch mutation of 'Green Giant'.

Asexual propagation of the new cultivar was first accomplished by the Inventor using stem cuttings in Meriden, Conn. in the 2015. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Leprechaun' as a unique cultivar of *Thuja*.

1. 'Leprechaun' exhibits a slow growing and compact plant habit.
2. 'Leprechaun' exhibits foliage that is soft in texture and dark green in color.
3. 'Leprechaun' exhibits very good cold hardiness without winter foliage bronzing. (withstood −20° F.).

4. 'Leprechaun' exhibits a small mature plant size; reaching an average of 2.74 m in height and 1.52 m in width.

The parent plant of 'Leprechaun', 'Green Giant', differs from 'Leprechaun' in having a much larger plant size, a faster growth rate, a less compact and less dense plant habit, and foliage that is coarser in texture. 'Leprechaun' can also be compared to the *Thuja* cultivars 'Excelsa' (not patented) and 'Steeplechase' (U.S. Plant Pat. No. 16,094). 'Excelsa' is similar to 'Leprechaun' in having an upright plant shape and good cold hardiness with foliage that does not turn bronze in color in winter. 'Excelsa' differs from 'Leprechaun' in having a larger plant size in being taller and wider, a faster growth rate, a less dense and looser branching habit, and coarser foliage. 'Steeplechase' is similar to 'Leprechaun' in having an upright plant shape and dense foliage. 'Steeplechase' differs from 'Leprechaun' in having a narrower and taller plant size, a faster growth rate, bushier shape, and finer foliage.

BRIEF DESCRIPTION OF THE DRAWINGS

The accompanying color photographs illustrate the overall appearance and distinct characteristics of the new *Thuja*. The photographs were taken of a four-year-old plant as grown outdoors in a 5-gallon container in Meriden, Conn.

Figure 1:
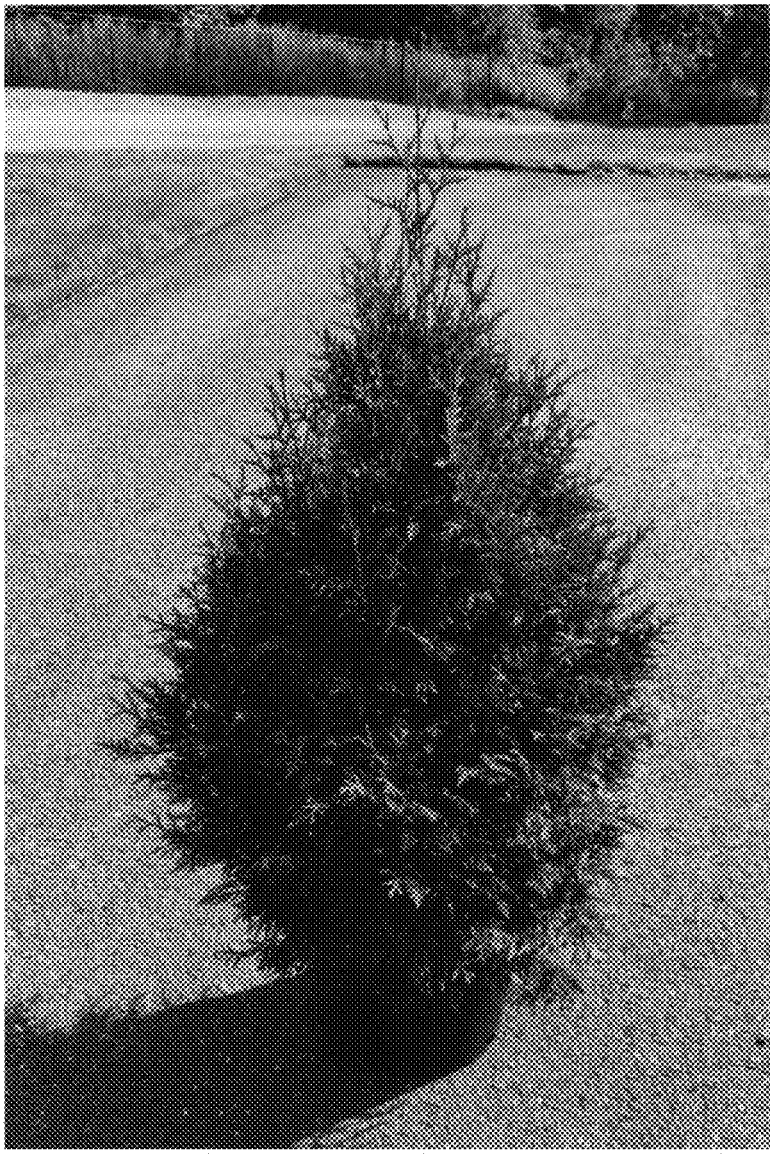
FIG. 1 provides an overall view of the plant habit of 'Leprechaun'.
Figure 2:
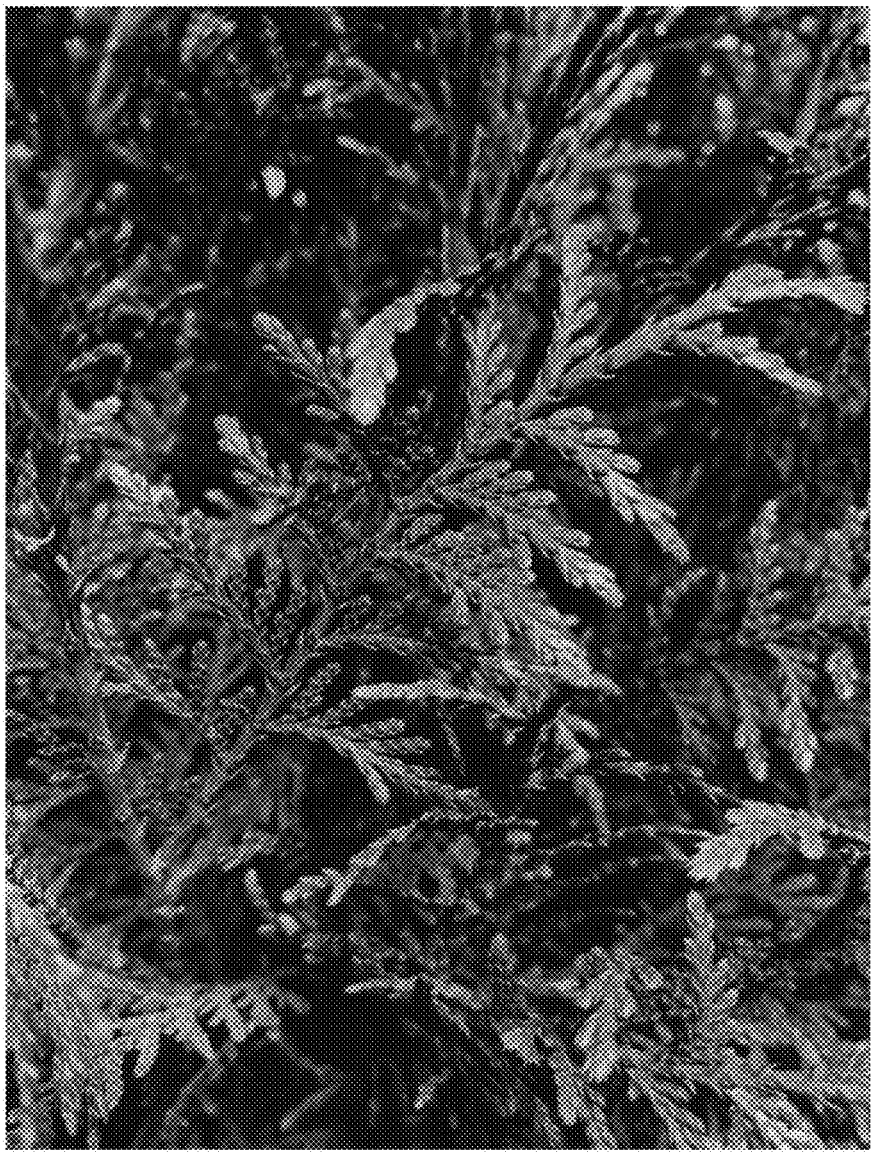
FIG. 2 provides a close-up view of the foliage of 'Leprechaun'.

The colors in the photographs are as close as possible with the photographic and printing technology utilized and the color values cited in the detailed botanical description accurately describe the colors of the new *Thuja*.

DETAILED BOTANICAL DESCRIPTION

The following is a detailed description of the new cultivar of four-year-old plants as grown outdoors in 5-gallon containers in Meriden, Conn. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Plant type.*—Evergreen tree.

*Plant habit.*—Upright, oval, compact.

*Plant size.*—87 cm in height and 58 cm in width for plants four years in age as grown in 5-gallon containers and an average of 2.74 m in height and 1.52 m in width as a ten year-old-plant in the landscape.

*Cold hardiness.*—At least to U.S.D.A. Zone 4.

*Diseases and pests.*—No susceptibility or resistance to diseases or pests has been observed.

*Root description.*—Fibrous, moderately thick, 164A in color.

*Propagation.*—Stem cuttings.

*Growth rate.*—Slow.

*Root development.*—8 to 10 weeks for root initiation, a plant 91 cm in height is produced in about 4 years from a rooted cutting.

Branch description:

*Branch quantity.*—6 main stems, 18 to 28 lateral branches from a main branch.

*Branch shape.*—Rounded.

*Branch size.*—Lateral branches; an average 35 cm in length and 5 mm in diameter, main branches; an average of 57 cm in length and 2.5 cm in width.

*Branch surface.*—Completely covered with scale-like leaves that are glossy and slightly rugose to smooth, scale-like leaves; whorled down the stems, 2 to 4 per whorl, 12 per 2 cm section, 8 mm in length, 4 mm in width, sharp acuminate apex, color when young is a blend of 143A and 139A, maturing to 165A in color, aging branches closer to base become dry and are 177A, apexes 164 in color.

*Branching.*—Dense, freely branching, compact.

*Branch arrangement.*—Alternate.

*Branch strength.*—Strong.

*Internode length.*—Average of 1 cm.

*Branch color.*—Young and mature branches; matches surface of scale-like leaf color, trunk; 197A.

*Branch aspect.*—Held upright.

Foliage description:

*Leaf arrangement.*—Alternate.

*Leaf attachment.*—Sessile.

*Leaf shape.*—Linear, scale-like.

*Leaf division.*—Simple.

*Leaf base.*—Cuneate.

*Leaf apex.*—Short apiculate.

*Leaf venation.*—Not distinguishable, coloration matches leaf coloration.

*Leaf margins.*—Entire.

*Leaf fragrance.*—Slight evergreen fragrance when crushed.

*Leaf surface.*—Upper and lower surfaces; glabrous and glossy.

*Leaf color.*—Newly emerging leaf tips 166B, young and mature upper and lower surfaces; 137A.

*Leaf size.*—Up to 16 cm in length and 6.5 cm in width, leaflets an average of 3.5 cm in length and 8 mm in width.

*Leaf quantity.*—Average of over 300 leaves per branch, average of 24 leaflets per leaf.

*Leaf glands.*—Average of 0.3 mm in length, 0.2 mm in width, rounded to oblong in shape, color matches leaf color.

Cone description: Neither male nor female cones have been observed to date.

It is claimed:

1. A new and distinct cultivar of *Thuja* plant named 'Leprechaun' as herein illustrated and described.

* * * * *